United States Patent

Obaidi

[11] Patent Number: 5,588,445
[45] Date of Patent: Dec. 31, 1996

[54] HEAD AND NECK PROTECTOR FOR CHILDREN

[76] Inventor: Hemayatullah S. Obaidi, 905 University Village Dr., Richardson, Tex. 75081

[21] Appl. No.: 651,776

[22] Filed: May 22, 1996

[51] Int. Cl.⁶ ............................................. A61F 5/37
[52] U.S. Cl. ................... 128/846; 128/870; 128/876; 128/857; 5/628; 5/655; 297/230.1
[58] Field of Search ............................. 128/845, 846, 128/857, 869, 870, 874, 875, 876; 5/655, 625, 628, 481; 297/230.1, 230.12, 485

[56] References Cited

U.S. PATENT DOCUMENTS

| | | | |
|---|---|---|---|
| 819,091 | 5/1906 | Smith | 128/846 |
| 3,724,453 | 4/1973 | Dixon | 128/870 |
| 3,856,349 | 12/1974 | Light | 297/230.12 |
| 4,034,748 | 7/1977 | Winner | 128/870 |
| 4,593,788 | 6/1986 | Miller | 128/870 |
| 5,056,533 | 10/1991 | Solano | 128/845 |
| 5,127,422 | 7/1992 | Colon | 128/870 |
| 5,261,134 | 11/1993 | Matthews | 5/655 |
| 5,310,245 | 5/1994 | Lyszczasz | 297/219.12 |
| 5,329,934 | 7/1994 | Bowman | 128/870 |
| 5,339,472 | 8/1991 | Lin | 5/631 |

*Primary Examiner*—Michael A. Brown
*Attorney, Agent, or Firm*—Joseph N. Breaux

[57] ABSTRACT

A head and neck protector including a flexible resilient back member sized to cover the back, shoulders and head of a child having a substantially smooth child contacting surface and constructed from a flexible mesh member surrounded by resilient foam and covered with a fabric covering; an adjustable torso strap assembly secured to the resilient back member; first and second adjustable shoulder straps; a removable sloped cushion member; and a cushion retaining strap forming a cushion retaining loop into which the sloped cushion member is inserted and held. In use, the back of a child is placed against the child contact surface and the straps secured about the child. The resilient flexible back support prevents rapid jerky movements that can cause back and neck injuries. In addition, the back support member and the sloped cushion member provide cushioning for the neck and head should the child fall backwards while attempting to sit or walk.

20 Claims, 1 Drawing Sheet

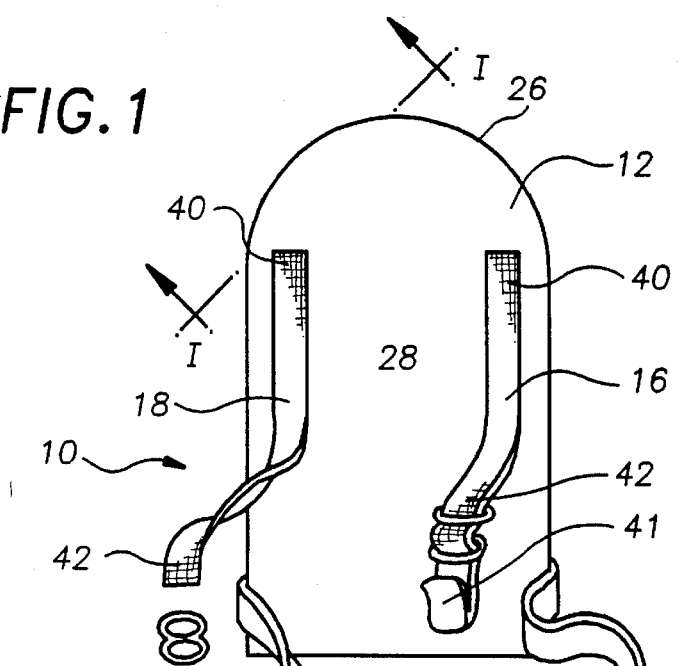
FIG. 1
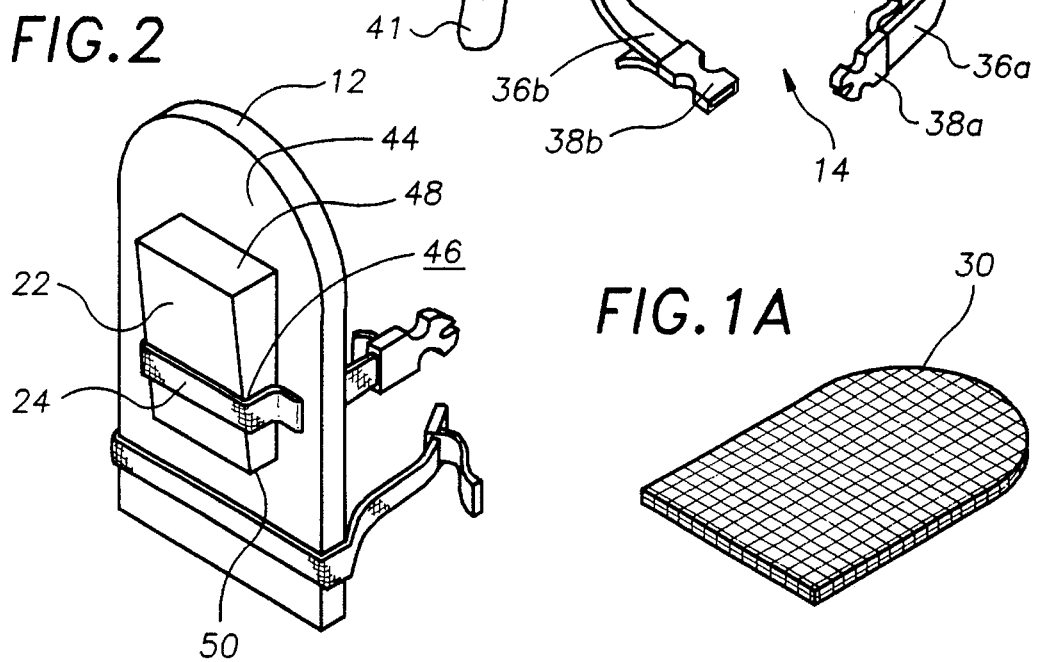
FIG. 2
FIG. 1A
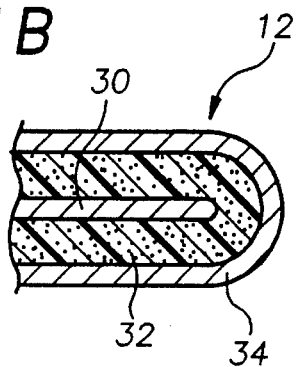
FIG. 1B

HEAD AND NECK PROTECTOR FOR CHILDREN

TECHNICAL FIELD

The present invention relates to neck and head protectors for infants and small children and more particularly to a head and neck protector for infants and small children having an adjustable shoulder and waist harness for securing a resilient back support member to a child or infant.

BACKGROUND ART

Infants and small children often fall because of poor muscle control when learning to walk or sit up. These falls can be dangerous and can result in serious head and neck injuries to the child. It would be a benefit, therefore, to have a protective device securable to the child or infant that could support and cushion the head and neck of a child or infant and protect the child or infant from head and neck injuries. It would also be a benefit if the protective device included a resilient back support member that flexed to allow movement of the child but that was sufficiently resilient to provide neck and head protection from falls.

GENERAL SUMMARY DISCUSSION OF INVENTION

It is thus an object of the invention to provide a head and neck protector that is securable to a child that supports and cushions the head and neck of a child or infant and protects the child or infant from head and neck injuries It is a further object of the invention to provide a head and neck protector that includes a resilient back support member that flexes to allow movement of the child but that is sufficiently resilient to provide neck and head protection from falls.

Accordingly, a head and neck protector for children is provided. The head and neck protector comprises a flexible resilient back support member, sized to cover the back, shoulders and head of a child, having a substantially smooth child contacting surface and constructed from a flexible mesh member surrounded by resilient foam and covered with a fabric covering; an adjustable torso strap assembly secured to the resilient back member including first and second adjustable length torso straps securable about the torso of a child; first and second adjustable shoulder straps secured to the child contacting surface, each of the first and second shoulder straps having a securing mechanism on a distal end thereof for securing the shoulder strap to one of the first and second torso straps; a removable sloped cushion member; and a cushion retaining strap forming a cushion retaining loop into which the sloped cushion member is inserted and held. In use, the back of a child is placed against the child contact surface. The torso strap assembly is then secured about the waist of the child, the shoulder straps placed over the shoulders and the securing mechanism used to secure the shoulder straps to the torsos straps. If it is desired to use the sloped cushion member, the sloped cushion member is inserted into the cushion retaining loop. Because the back support member is flexible, the child is free to bend and move. In addition, the resilient flexible back support member prevents rapid jerky movements that can cause back and neck injuries. In addition, the back support member and the sloped cushion member provide cushioning for the child's neck and head should the child fall backwards while attempting to sit or walk.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1 is a front view of an exemplary embodiment of the head and neck protector of the present invention showing the resilient back support member including the child contact surface, the adjustable torso strap assembly, and the adjustable shoulder straps.

FIG. 1A is a perspective view of the flexible mesh member in isolation.

FIG. 1B is a cross sectional detail view through the exemplary resilient back support member of FIG. 1 along the line I—I showing the central flexible mesh member, foam padding, and cloth outer covering.

FIG. 2 is a perspective view of the head and neck protector of FIG. 1 showing the back side of the resilient back support member, the removable cushion member and the cushion retaining strap.

EXEMPLARY MODE FOR CARRYING OUT THE INVENTION

FIG. 1 shows an exemplary embodiment of the head and neck protector for children of the present invention generally designated by the numeral 10. Head and neck protector 10 includes a back support member 12, a torso harness assembly generally designated by the numeral 14, a first adjustable shoulder strap 16, a second adjustable shoulder strap 18, a removable sloped cushion member 22 (shown in FIG. 2), and a cushion retaining strap 24 (shown in FIG. 2).

In this embodiment, back support member 12 is about fourteen (14") inches long, nine (9") inches wide and has a rounded top edge 26. A back contacting surface 28 is provided of the same dimensions as back support member. In this embodiment, back contacting surface 28 is a section of cloth material. With reference to FIG. 1A, back support member 12 is constructed from a flexible mesh member 30 formed from a section of flexible nylon mesh material having a thickness of about one-eight (⅛") inch that is cut in the same shape as back support member 12 but is about one-half (½") smaller in length and width. With reference to FIG. 1B, flexible mesh member 30 is surrounded by resilient plastic foam 32 that is in turn covered with a cloth outer covering 34.

With reference once again to FIG. 1, adjustable torso strap assembly 14 includes first and second adjustable length torso straps 36a, 36b that are formed from nylon strapping material. Torso straps 36a, 36b are interconnectable about the torso of the child or infant and secured together with a conventional strap fastener assembly including a male portion 38a, and a female portion 38b.

First and second adjustable shoulder straps 16,18 are each stitched to contact surface 28 at one end 40 thereof and provided with clips 41 at a second end 42 thereof. In use, clips 41 are secured to first and second torso straps 36a, 36b after first and second shoulder straps 16,18 have been positioned over the shoulders of the child or infant.

FIG. 2 shows cushion retaining strap 24 stitched to the backside 44 of back support member 12 at both ends to form a cushion retaining loop 46. In this embodiment, cushion retaining strap 24 is a length of nylon strapping material. Sloped cushion member 22 is a wedge shaped section of resilient plastic foam that has been cover with a fabric cover. Sloped cushion member 22 slopes from a thickness of two (2") inches at one end 48 to a thickness of one (1") inch at a second end 50.

With general reference to FIGS. 1,1A, 1B, and 2, Head and neck protector 10 is used as follows. The back of a child is placed against child contact surface 28 and torso strap assembly 14 secured about the waist of the child. First and second shoulder straps 16,18 are then placed over the shoulders of the child and clips 41 clipped to first and second torso straps 36a,36b. The lengths of first and second shoulder straps 16,18 and first and second torso straps 36a, 36b are then adjusted to snugly secure the child to flexible back support member 12. If it is desired to use sloped cushion member 22, sloped cushion member 22 is inserted into cushion retaining loop 46. The child is then free to crawl walk or sit up in the normal fashion. Resilient flexible back support 12 prevents rapid jerky movements that can cause back and neck injuries. In addition, back support member 12 and sloped cushion member 22 provide cushioning for the neck and head shoulders of the child should the child fall backwards while attempting to sit or walk.

It can be seen from the preceding description that a head and neck protector for a child or infant has been provided that is securable to a child, that supports and cushions the head and neck of a child or infant, that protects the child or infant from head and neck injuries, and that includes a resilient back support member that flexes to allow movement of the child but that is sufficiently resilient to provide neck and head protection from falls.

It is noted that the embodiment of the head and neck protector described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A head and neck protector comprising:

a flexible resilient back member sized to cover the back shoulders and head of a child having a substantially smooth child contacting surface and constructed from a flexible mesh member surrounded by resilient foam and covered with a fabric covering;

an adjustable torso strap assembly secured to said resilient back member including first and second adjustable length torso straps securable about said torso of a child;

first and second adjustable shoulder straps secured to said child contacting surface, each of said first and second shoulder straps having a securing mechanism on a distal end thereof for securing said shoulder strap to one of said first and second torso straps;

a removable sloped cushion member; and a cushion retaining strap attached to said back member and forming a cushion retaining loop into which said sloped cushion member is inserted and held.

2. The head and neck protector of claim 1, wherein:

said flexible mesh member is formed from a section of nylon mesh material that is cut in the same shape as back support member.

3. The head and neck protector of claim 2, wherein:

said back support member has a rounded top edge.

4. The head and neck protector of claim 3 wherein:

said first and second adjustable shoulder straps are each stitched to contact surface at one end thereof and provided with clips at a second end thereof.

5. The head and neck protector of claim 4 wherein:

said cushion retaining strap is stitched to a backside of back support member at both ends thereof to form said cushion retaining loop; and said sloped cushion member is a wedge shaped section of plastic foam that is covered with a fabric cover.

6. The head and neck protector of claim 5 wherein:

said sloped cushion member slopes from a thickness of two (2") inches at one end thereof to a thickness of one (1") inch at a second end thereof.

7. The head and neck protector of claim 4 wherein:

said sloped cushion member slopes from a thickness of two (2") inches at one end thereof to a thickness of one (1") inch at a second end thereof.

8. The head and neck protector of claim 3 wherein:

said cushion retaining strap is stitched to a backside of back support member at both ends thereof to form said cushion retaining loop; and said sloped cushion member is a wedge shaped section of plastic foam that is covered with a fabric cover.

9. The head and neck protector of claim 3 wherein:

said sloped cushion member slopes from a thickness of two (2") inches at one end thereof to a thickness of one (1") inch at a second end thereof.

10. The head and neck protector of claim 2 wherein:

said first and second adjustable shoulder straps are each stitched to contact surface at one end thereof and provided with clips at a second end thereof.

11. The head and neck protector of claim 2 wherein:

said cushion retaining strap is stitched to a backside of back support member at both ends thereof to form said cushion retaining loop; and said sloped cushion member is a wedge shaped section of plastic foam that is covered with a fabric cover.

12. The head and neck protector of claim 2 wherein:

said sloped cushion member slopes from a thickness of two (2") inches at one end thereof to a thickness of one (1") inch at a second end thereof.

13. The head and neck protector of claim 1, wherein:

said back support member has a rounded top edge.

14. The head and neck protector of claim 13 wherein:

said first and second adjustable shoulder straps are each stitched to contact surface at one end thereof and provided with clips at a second end thereof.

15. The head and neck protector of claim 13 wherein:

said cushion retaining strap is stitched to a backside of back support member at both ends thereof to form said cushion retaining loop; and said sloped cushion member is a wedge shaped section of plastic foam that is covered with a fabric cover.

16. The head and neck protector of claim 13 wherein:

said sloped cushion member slopes from a thickness of two (2") inches at one end thereof to a thickness of one (1") inch at a second end thereof.

17. The head and neck protector of claim 1 wherein:

said first and second adjustable shoulder straps are each stitched to contact surface at one end thereof and provided with clips at a second end thereof.

18. The head and neck protector of claim 1 wherein:

said cushion retaining strap is stitched to a backside of back support member at both ends thereof to form said cushion retaining loop; and said sloped cushion member is a wedge shaped section of plastic foam that is covered with a fabric cover.

19. The head and neck protector of claim 1 wherein:

said sloped cushion member slopes from a thickness of two (2") inches at one end thereof to a thickness of one (1") inch at a second end thereof.

20. The head and neck protector of claim 1 wherein:

said first and second adjustable shoulder straps are each stitched to contact surface at one end thereof and provided with clips at a second end thereof;

said cushion retaining strap is stitched to a backside of back support member at both ends thereof to form said cushion retaining loop;

said sloped cushion member is a wedge shaped section of plastic foam that is covered with a fabric cover; and said sloped cushion member slopes from a thickness of two (2") inches at one end thereof to a thickness of one (1") inch at a second end thereof.

* * * * *